US012599150B2

(12) United States Patent
Hatta et al.

(10) Patent No.: US 12,599,150 B2
(45) Date of Patent: Apr. 14, 2026

(54) HIGHLY EMULSIFIABLE ALBUMEN HYDROLYSATE

(71) Applicants:AMANO ENZYME INC., Nagoya (JP); Hajime Hatta, Uji (JP); ISE FOODS. INC., Kounosu (JP)

(72) Inventors: Hajime Hatta, Uji (JP); Mayuko Takagi, Shiroi (JP); Sakiko Sho, Kyoto (JP); Saki Nagata, Nagaokakyo (JP); Shuntaro Ise, Tokyo (JP); Yasumi Horimoto, Guelph (CA); Yu Wang, Rennes (FR)

(73) Assignees: Amano Enzyme Inc., Nagoya (JP); Hajime Hatta, Kyoto (JP)

( * ) Notice: Subject to any disclaimer, the term of this patent is extended or adjusted under 35 U.S.C. 154(b) by 385 days.

(21) Appl. No.: 17/342,726

(22) Filed: Jun. 9, 2021

(65) Prior Publication Data

US 2021/0289811 A1 Sep. 23, 2021

Related U.S. Application Data

(62) Division of application No. 15/313,592, filed as application No. PCT/JP2014/064169 on May 28, 2014, now abandoned.

(51) Int. Cl.
*A23J 1/08* (2006.01)
*A23J 1/09* (2006.01)
(Continued)

(52) U.S. Cl.
CPC . *A23J 1/08* (2013.01); *A23J 1/09* (2013.01); *A23J 3/34* (2013.01); *A23K 10/10* (2016.05);
(Continued)

(58) Field of Classification Search
CPC ....... A23J 1/08; A23J 1/09; A23J 3/34; A23K 10/10; A23L 15/25; A23L 35/10
See application file for complete search history.

(56) References Cited

U.S. PATENT DOCUMENTS

| | | | |
|---|---|---|---|
| 3,970,520 A | 7/1976 | Feldman et al. | |
| 2010/0112131 A1 | 5/2010 | Qiao et al. | |
| 2013/0251851 A1 | 9/2013 | Watabe et al. | |

FOREIGN PATENT DOCUMENTS

| | | |
|---|---|---|
| DE | 294 855 A5 | 10/1991 |
| EP | 0087247 A2 | 8/1983 |

(Continued)

OTHER PUBLICATIONS

JP S6058056 Machine Translation 1985 (Year: 1985).*

(Continued)

*Primary Examiner* — Felicia C Turner
(74) *Attorney, Agent, or Firm* — Troutman Pepper Locke LLP

(57) ABSTRACT

The present invention addresses the problem of providing an albumen hydrolysate that has emulsifiability, emulsion stability and heat coagulability. An albumen hydrolysate obtained by hydrolysis of albumen with a protease, wherein the dry weight of a precipitate formed by adding nine times the amount of 0.4 M trichloroacetic acid (TCA) to the albumen hydrolysate is 60% or more relative to the dry weight of albumen treated in the same manner.

11 Claims, 7 Drawing Sheets

(51) Int. Cl.

| | | |
|---|---|---|
| *A23J 3/34* | (2006.01) |
| *A23K 10/10* | (2016.01) |
| *A23L 15/00* | (2016.01) |
| *A23L 29/10* | (2016.01) |
| *A23L 35/00* | (2016.01) |
| *A61K 8/64* | (2006.01) |
| *A61Q 19/00* | (2006.01) |

(52) U.S. Cl.

CPC .............. *A23L 15/00* (2016.08); *A23L 15/25* (2016.08); *A23L 29/10* (2016.08); *A23L 35/10* (2016.08); *A61K 8/64* (2013.01); *A61Q 19/00* (2013.01); *A23V 2002/00* (2013.01); *A61K 2800/10* (2013.01)

(56) References Cited

FOREIGN PATENT DOCUMENTS

| | | | | | |
|---|---|---|---|---|---|
| GB | 2134117 | A | * | 8/1984 | ................ A23J 3/00 |
| JP | 61-85170 | A | | 4/1986 | |
| JP | 61-132157 | A | | 6/1986 | |
| JP | S6147504 | B2 | | 10/1986 | |
| JP | 62-48358 | A | | 3/1987 | |
| JP | 2-135097 | A | | 5/1990 | |
| JP | 2-218796 | A | | 8/1990 | |
| JP | 3-249935 | A | | 11/1991 | |
| JP | 9-9860 | A | | 1/1997 | |
| JP | 2005-117915 | A | | 5/2005 | |
| JP | 2006-101801 | A | | 4/2006 | |
| JP | 2006-187277 | A | | 7/2006 | |
| JP | 2006-320315 | A | | 11/2006 | |
| JP | 2007-167041 | A | | 7/2007 | |
| JP | 4138889 | B2 | | 8/2008 | |
| JP | 2014-103957 | A | | 6/2014 | |
| WO | 94/25580 | A1 | | 11/1994 | |
| WO | WO-2005074703 | A1 | * | 8/2005 | .............. A23J 3/341 |
| WO | WO-2007144398 | A1 | * | 12/2007 | ............... A23J 1/08 |
| WO | 2012/146717 | A1 | | 11/2012 | |

OTHER PUBLICATIONS

Kato, A et al., "Relationship between Surface Functional Properties and Flexibility of Proteins Detected by the Protease Susceptibility," J. Agric. Food Chem., 33, 1985, pp. 931-934.

International Search Report mailed Aug. 5, 2014, issued for PCT/JP2014/064169.

Supplementary European Search Report dated Nov. 17, 2017, issued for the European patent application No. 14892965.6.

U. Behnke et al., "Enzymatic Modification of Egg-White Protein and Some of Its Functional Properties", Nahrung—Food, VCH Verlagsgesellschaft, Weinheim, DE, vol. 30, No. 314, Jan. 1, 1986, pp. 319-326.

Office Action dated Aug. 17, 2018, issued for the European patent application No. 14892965.6.

Piske et al. (DD 294855 Derwent Abstract) 2 pages (Year: 1991).

Guerrero et al. JP 07289198 Nov. 7, 1995 Derwent Abstract (Year: 1995).

* cited by examiner

Compressive deformation rate (%)

Albumen

*FIG. 2*                    Sample 1

Load
[gf/cm²]

Compressive deformation rate (%)

*Fig. 3*                 Sample 2

*Fig. 4*                                    Sample 3

Sample 4

HIGHLY EMULSIFIABLE ALBUMEN HYDROLYSATE

TECHNICAL FIELD

The present invention relates to an albumen hydrolysate having high emulsifiability, emulsion stability and heat coagulability and a process for producing the same. Also, the invention relates to an emulsifier and an emulsion stabilizer comprising the albumen hydrolysate, and various processed foods.

BACKGROUND ART

Chicken egg has traditionally been utilized as a food and a food material (processed egg). Humankind has developed a number of egg dishes and egg-utilized foods and made use of egg at rich dietary life. This is because egg has excellent nutritional property and has various functional properties suitable for cooking and food processing.

The main functional properties of processed egg utilized in the field of foods include the heat coagulability and foaming property of albumen and the emulsifiability of yolk. The addition of physical manipulations such as heating, foaming and emulsification to egg causes a structural change in its albumen protein or yolk lipoprotein to develop their respective functional properties.

These functional properties are developed as the water retaining property, air retaining property and oil retaining property of processed egg. At present, in the field of foods, the heat coagulability of albumen is utilized mainly for fish paste products, livestock paste products, noodles and the like; the foaming property of albumen is utilized for cakes, meringue and the like; and the emulsifiability of yolk is utilized for mayonnaise, dressing and the like.

Albumen comprises 90% of moisture, 10% of a protein and minor amounts of vitamins and minerals, and is lipid-free. Albumen comprises about 40 kinds of proteins. Among the proteins, albumen comprises 54% of ovalbumin, which is the main protein, and then 12% of ovotransferrin, 11% of ovomucoid, 4% of G2 globulin and G3 globulin, respectively, 3.5% of ovomucin, 3.4% of lyzozyme, 1.5% of ovoinhibitor, and 1.0% of ovoglycoprotein. Those albumen proteins have a high nutritional value and an amino acid score of 100, and their protein efficiency ratio (PER) and biological value (BV) % are comparable to those values of breast milk.

Albumen has excellent heat coagulability and foaming property as functions as processed egg, but hardly has emulsifiability.

Conventionally, amphipathic substances having a hydrophilic group and a hydrophobic group in the molecule have been known to have excellent emulsifiability. As for food proteins, milk casein and wheat gluten have been known as amphipathic substances and exhibit strong emulsifiability. These proteins have good balance between hydrophilic amino acids and hydrophobic amino acids on their molecular surface and exhibit excellent emulsifiability. On the other hand, albumen proteins are also amphipathic substances comprising hydrophilic and hydrophobic amino acids. However, albumen proteins normally comprise hydrophobic amino acids localized inside their molecule and hydrophilic amino acids localized on their molecular surface, and form a colloidal state as a stable water soluble protein. Therefore, albumen proteins hardly exhibit emulsifiability. However, when albumen proteins are denatured so that the localization of hydrophilic and hydrophobic amino acids in their molecule is disrupted, emulsifiability can be developed.

For example, it has been reported that, when the albumen protein ovalbumin is denatured in a dilute concentration of 0.5% or less, at an alkali pH which is distant from the isoelectric point, or under the conditions for causing no heat gelation with low ionic strength to expose the internal hydrophobicity to the surface, thereby enhancing the surface hydrophobicity of ovalbumin, the foaming property and emulsifiability are remarkably enhanced (Non-Patent Literature 1).

From the above finding, when albumen proteins are heated and denatured, the hydrophobicity of the protein molecular surface can be enhanced, thereby providing excellent emulsifiability. However, normal albumen, when heated, begins to become cloudy from 60° C., begins to softly coagulate, and is hard-gelled at 80° C. or higher. Since the heat denaturation of albumen proteins causes gelation, the proteins are insolubilized even when the albumen gel is ground. Therefore, the improvement in emulsifying capacity cannot be expected.

In recent years, attention has been paid to the preparation of a peptide having good digestive absorbency or a peptide having physiological activity by hydrolysis of albumen proteins with a protease (Patent Literatures 1 to 3). In this case, albumen proteins exhibit no coagulability even when hydrolyzed and heated, and the water soluble peptides obtained therefrom exhibit emulsifiability due to their amphipathic structure. The emulsifiability, however, is not so strong and at most about twice as high as that of the albumen liquid before hydrolysis. Besides, the emulsion stability is bad.

In addition to such features of albumen, as for processed egg, yolk is in great demand and used in mayonnaise and western confectioneries, and the consumption thereof tends to increase. Whereas, the consumption of albumen decreases along with weak demand of fish paste products, and a large amount of surplus albumen is now frozen for storage. The frozen storage cost imposes great burden on chicken egg processors, and new use development of albumen is demanded.

CITATIONS LIST

Patent Literatures

Patent Literature 1: JP 2005-117915 A
Patent Literature 2: JP 2007-167041 A
Patent Literature 3: JP 4138889 B

Non Patent Literature

Non Patent Literature 1: Kato, A et al.: J. Agric. Food Chem., 33, 931, 1985

SUMMARY OF INVENTION

Technical Problems

An object of the present invention is to provide an albumen processed product to which emulsifiability and emulsion stability are newly imparted by modifying the functionality of albumen and a process for producing the same, an emulsifier and an emulsion stabilizer comprising the albumen processed product, and a processed food using the same.

Solutions to Problems

The present inventors made earnest studies in light of the above problem, and have found that, in the hydrolysis of an albumen liquid with a protease, when the albumen liquid is decomposed to such a level that the heat coagulability completely disappears, the emulsifiability is not so strong, and when the albumen liquid is decomposed to such a level that the heat coagulability slightly remains but is weak, surprising emulsifiability and emulsion stability are unexpectedly obtained. As a result of further studies based on these findings, the present invention has been completed.

Specifically, the present invention provides the following matter.

[1] An albumen hydrolysate obtained by hydrolysis of albumen with a protease, wherein the dry weight of a precipitate formed by adding nine times the amount of 0.4 M trichloroacetic acid (TCA) to the albumen hydrolysate is 60% or more relative to the dry weight of albumen treated in the same manner.

[2] The albumen hydrolysate according to [1], wherein the protease is a protease extracted from a microorganism belonging to the genus *Bacillus* or *Aspergillus*.

[3] The albumen hydrolysate according to [2], wherein the microorganism belonging to the genus *Bacillus* is *Bacillus stearothermophilus*.

[4] The albumen hydrolysate according to [2], wherein the microorganism belonging to the genus *Aspergillus* is *Aspergillus oryzae*.

[5] The albumen hydrolysate according to any one of [1] to [4], wherein the absorbance (500 nm), when the albumen hydrolysate is emulsified with an equal amount of an oil and the emulsified liquids immediately after the emulsification and after the elapse of one hour are diluted to 200 times with a 0.1% SDS liquid, is 0.1 or more.

[6] An emulsifier comprising the albumen hydrolysate according to any one of [1] to [5] as an active ingredient.

[7] An emulsion stabilizer comprising the albumen hydrolysate according to any one of [1] to [5] as an active ingredient.

[8] A processed food comprising the albumen hydrolysate according to any one of [1] to [5].

[9] A process for producing an albumen hydrolysate, comprising the step of hydrolyzing albumen with a protease at 45° C. to 70° C. and a pH of 6 to 9 for 0.5 hour to 2 hours.

[10] The process for producing an albumen hydrolysate according to [9], further comprising the step of heating the hydrolyzed albumen at 75° C. to 100° C. for 5 minutes to 30 minutes.

Advantageous Effects of Invention

The albumen decomposed product of the present invention not only has less bitterness and good flavor, but also has emulsifiability, emulsion stability and thermal coagulability together, and can be advantageously utilized as a highly-safe material of natural origin, for example, in foods and beverages, feed, cosmetics and medicaments.

Also, albumen-based mayonnaise and dressing, albumen ice cream, albumen mousse, etc. can be prepared, and non-fat or low-fat, low-cholesterol and high-protein emulsified foods can be produced.

The emulsifier in the present invention not only has excellent emulsifiability, but also is very highly safe, and thus can be used safely alone as an emulsifier for foods, beverages, feed, foods for fishes and shellfishes and aquarium fishes, cosmetics, medicaments and other various target products which require emulsifiability, or together with other emulsifiers.

DESCRIPTION OF EMBODIMENTS

Figure 1:
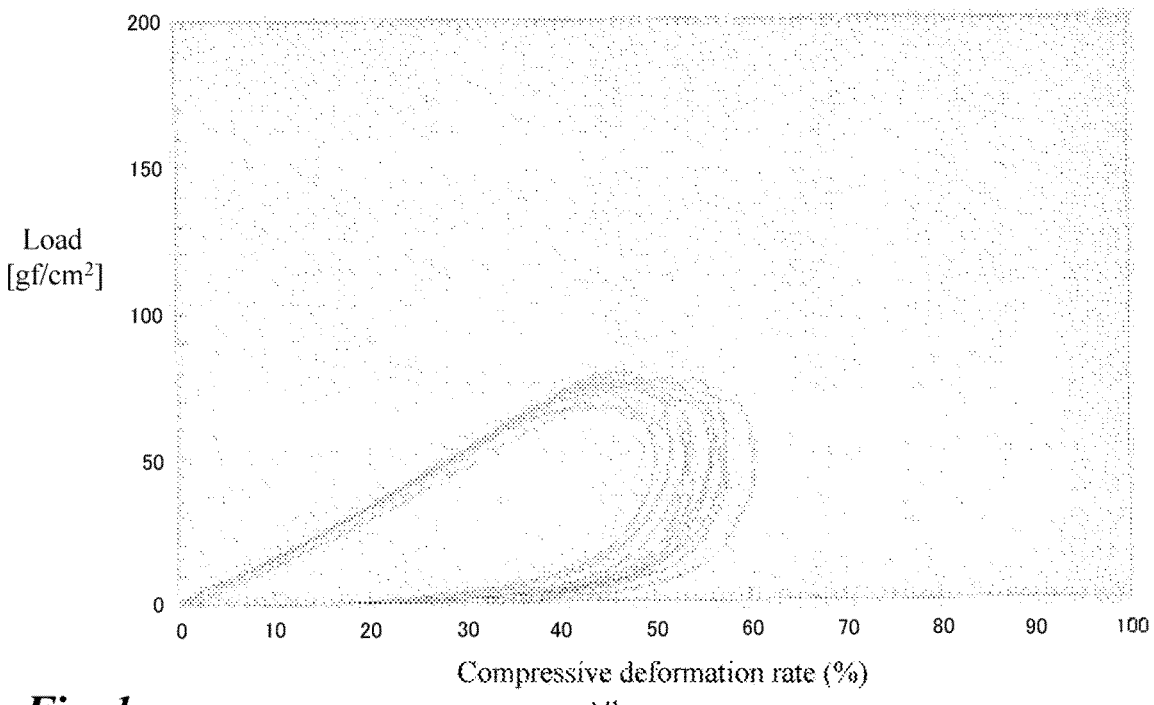
FIG. 1 shows a rupture deformation curve of albumen.
Figure 2:
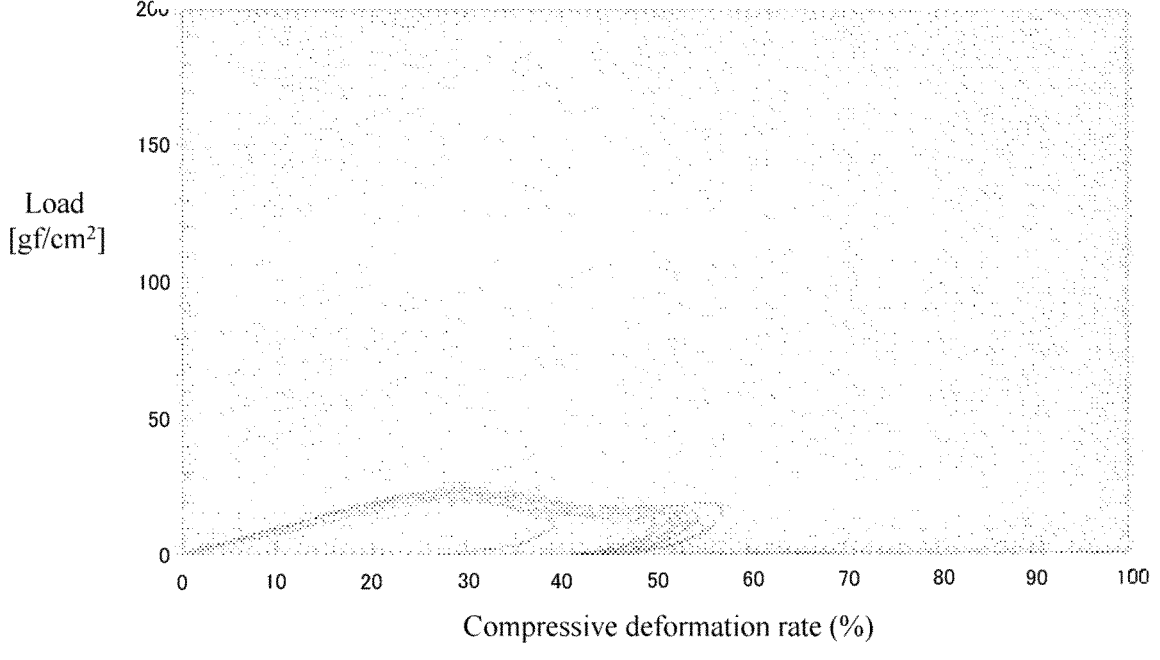
FIG. 2 shows a rupture deformation curve of Sample 1.
Figure 3:
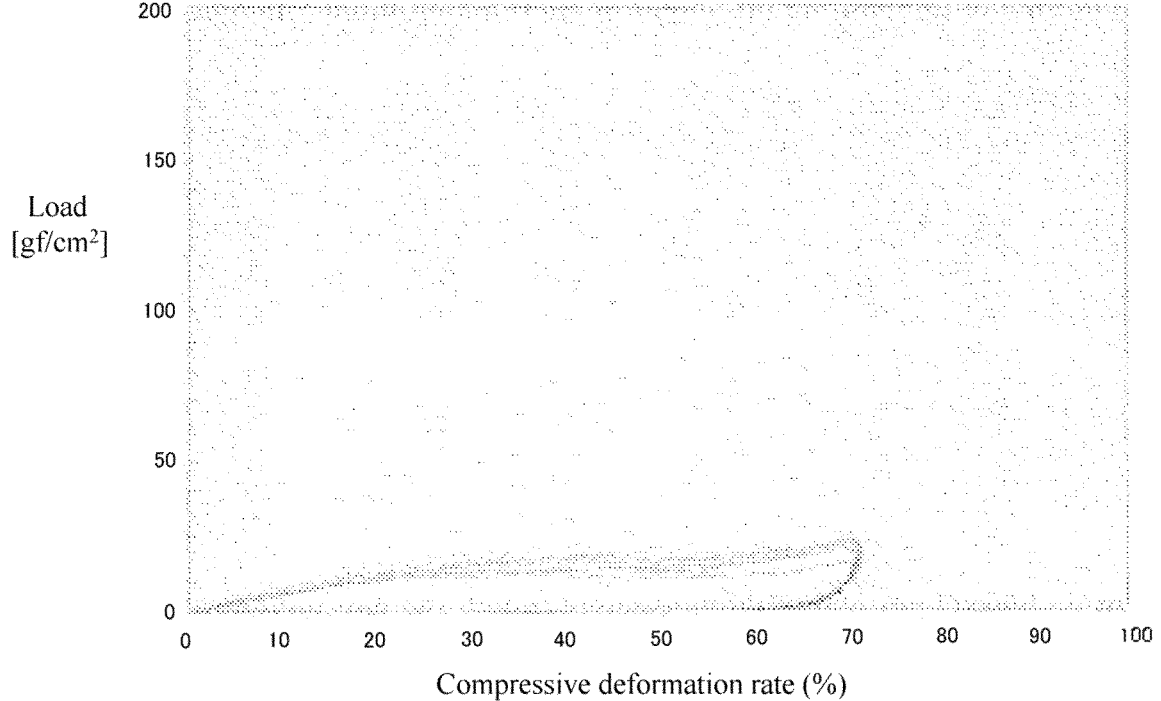
FIG. 3 shows a rupture deformation curve of Sample 2.
Figure 4:
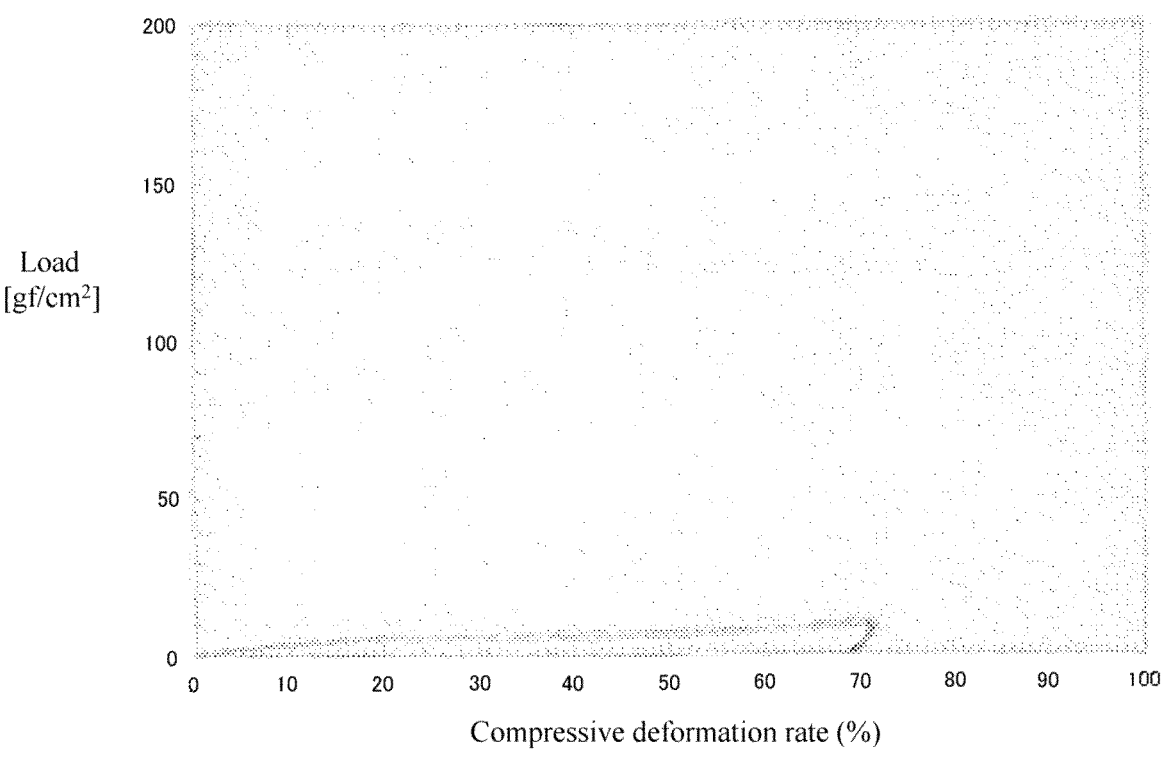
FIG. 4 shows a rupture deformation curve of Sample 3.
Figure 5:
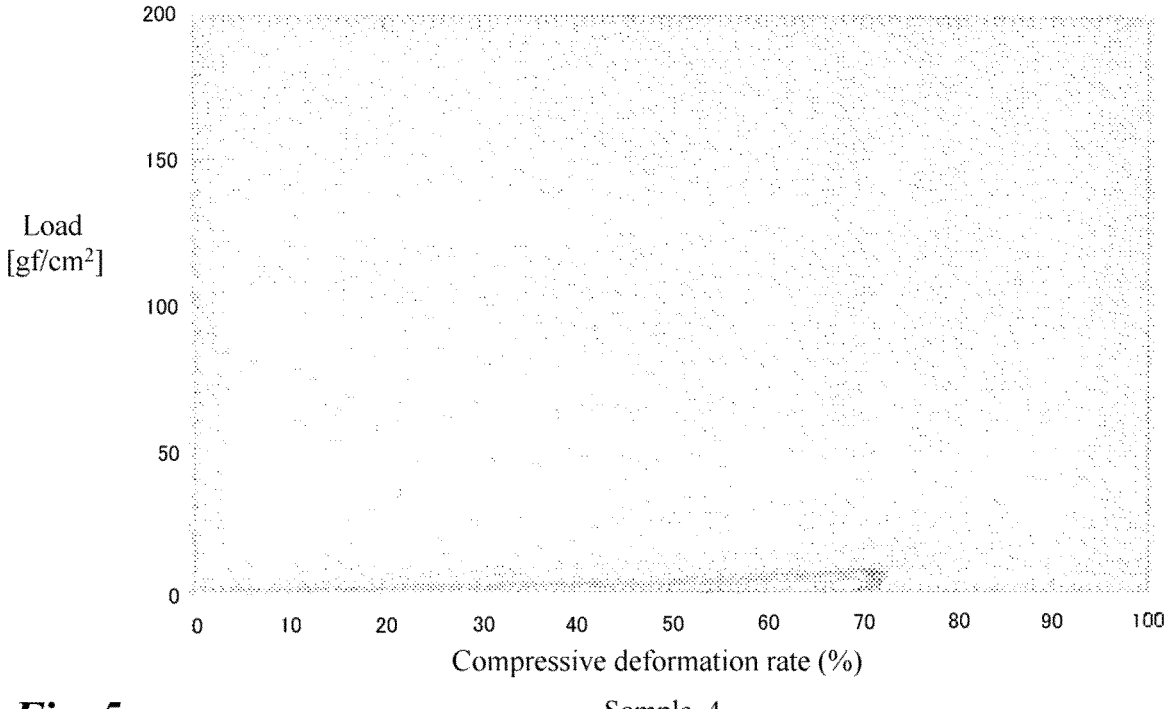
FIG. 5 shows a rupture deformation curve of Sample 4.

The present invention relates to an albumen hydrolysate obtained by hydrolysis of albumen with a protease, characterized in that the dry weight of a precipitate formed by adding nine times the amount of 0.4 M trichloroacetic acid (TCA) to the albumen hydrolysate is 60% or more relative to the dry weight of albumen treated in the same manner (hereinafter abbreviated as "the albumen hydrolysate according to the present invention" in some cases).

In the present invention, albumen normally includes raw albumen liquid separated from chicken egg, heat-sterilized albumen liquid, frozen albumen liquid, sterilized frozen albumen liquid, and powder albumen. Preferably, raw albumen liquid and heat-sterilized albumen liquid are used from the viewpoint of processability. Also, the utilization of an albumen liquid homogenized by high-pressure homogenizer treatment or the like to enhance the heat coagulation temperature is preferred also from the viewpoint of enzymatic hydrolysis temperature.

The protease used in the present invention is one, or a combination of two or more, of animal-derived enzymes such as pepsin, (chymo)trypsin and cathepsin; plant-derived enzymes such as papain, bromelin and ficin; and known enzymes such as various microorganism-derived proteases. Since protease inhibitors such as ovomucoid, ovoinhibitor and ovostatin are present in albumen, heat resistant proteases which work at temperatures at which the protease inhibitory activity of these albumen proteins is hard to work, i.e., 55° C. to 75° C. are preferably utilized.

Among them, microorganism-derived proteases are preferred, and proteases derived from microorganisms belonging to the genus *Bacillus* and proteases derived from microorganisms belonging to the genus *Aspergillus* are preferred as producing less bitter amino acids and peptides. More preferably, proteases derived from *Bacillus stearothermophilus* and proteases derived from *Aspergillus oryzae* can be used.

The method for extracting a protease from a microbial cell used in the present invention is not particularly limited, and a common enzyme extraction method can be applied. Various commercial protease preparations may also be used.

The amount of the protease to be added is appropriately determined depending on the kind of enzyme and the enzymatic activity. For example, in the case of a commercial protease preparation which is an enzyme agent having enzymatic activity of 50,000 to 100,000 units/g as measured with normal milk casein as a substrate, the protease preparation is added in an amount of normally 0.1% by weight to 0.8% by weight, preferably 0.1% by weight to 0.4% by weight, more preferably 0.1% by weight to 0.2% by weight relative to the entire albumen weight from the viewpoint of obtaining the desired decomposition degree.

For example, in the case of a heat resistant protease preparation extracted from microbial cells of *Bacillus stearothermophilus* (Thermoase PC10 manufactured by Amano Enzyme Inc., 90,000 units/g), the protease preparation is added in an amount of normally 0.1% by weight to 0.8% by weight, preferably 0.1% by weight to 0.4% by weight, more preferably 0.1% by weight to 0.2% by weight relative to the entire albumen weight. Also, in the case of an acidic protease preparation derived from *Aspergillus oryzae* (Protease M "AMANO" SD, 40,000 units/g), the protease preparation is added in an amount of for example 0.05% by weight to 0.5% by weight, preferably 0.1% by weight to 0.2% by weight relative to the entire albumen weight.

In the present invention, the hydrolysis treatment of albumen with a protease is conducted as follows.

The temperature for adding a protease to albumen is a temperature at which an albumen protease inhibitor is hard to work and the heat coagulation of albumen would not start, avoiding the proliferation temperature for bacteria. The protease is added to albumen normally at 45° C. to 60° C., preferably at 50° C. to 60° C., more preferably at 50° C. to 55° C., and hydrolysis is conducted for 10 minutes to 1 hour, preferably 10 to 30 minutes. The above hydrolysis is conducted as pre-hydrolysis, and the albumen liquid may be further warmed for hydrolysis. The warming temperature at this time is, for example, 60° C. to 80° C., preferably 60° C. to 70° C., more preferably 63° C. to 67° C.

Known methods can be applied as heating means, and there can be used, for example, indirect heating methods using jacketed tanks, plate heaters, shell-and-tube type heat exchangers and the like; and direct heating methods using Joule heating devices. From the viewpoint of precise control of the albumen liquid temperature, a shell-and-tube type heat exchanger or a Joule heating device is preferably used.

The hydrolysis may be conducted at a pH optimum for the enzyme to be used, and is conducted normally at a pH of 6 to 9, preferably at a pH of 6 to 8.5, more preferably at a pH of 6 to 8, most preferably at a pH of 6 to 7.5, from the viewpoint of avoiding pHs around the isoelectric point (around pH 5) for enhancing the solubility of the albumen proteins, and suppressing the alkali denaturation of the albumen proteins.

Hydrochloric acid, carbonic acid, phosphoric acid, acetic acid, citric acid, sodium carbonate, sodium hydrogen carbonate and sodium hydroxide are normally used for pH adjustment, and citric acid and phosphoric acid and sodium salts thereof are preferably utilized.

The hydrolysis treatment time is normally 0.5 hours to 4.0 hours, preferably 0.5 hours to 2 hours, more preferably 0.5 hours to 1 hour at a temperature optimum for the enzyme to be used, from the viewpoint of the emulsifiability, emulsion stability and heat coagulability.

Specifically, there is a method comprising warming preliminarily-warmed albumen at 50° C. to 55° C.; adding a protease thereto; hydrolyzing the mixture for 10 minutes to 30 minutes; further increasing the temperature to 63° C. to 67° C. for hydrolysis for 0.5 hours to 1 hour; and thereafter deactivating the enzyme through further warming, thereby obtaining the albumen hydrolysate according to the present invention. The waning temperature for deactivation of the enzyme is for example 75° C. to 100° C., preferably 80° C.

to 100° C., further preferably 80° C. to 95° C., most preferably 80° C. to 90° C. The enzyme deactivation treatment time is for example 5 minutes to 30 minutes, preferably 5 minutes to 20 minutes, more preferably 5 minutes to 10 minutes.

The thus-obtained albumen hydrolysate according to the present invention has a white cream- or slurry-like shape. The albumen hydrolysate according to the present invention may be homogenized under a high pressure condition. Alternatively, powdered or granular dried albumen hydrolysates obtained by applying drying treatment such as freeze drying or spray drying are also encompassed in the present invention.

The albumen hydrolysate according to the present invention is characterized in that the dry weight of a precipitate formed by adding nine times the amount of 0.4 M trichloroacetic acid (TCA) to the albumen hydrolysate is 60% or more relative to the dry weight of a precipitate formed by treating albumen in the same manner.

Specifically, when 9 parts by weight of 0.4M TCA is added to 1 part by weight of the albumen hydrolysate according to the present invention for precipitation, the dry weight of the thus-formed precipitate is 60% by weight or more, preferably 65% to 85% by weight, more preferably 70% to 80% by weight relative to the dry weight of the entire precipitate of albumen. Here, an albumen liquid is indicated as an example of the index albumen.

The substance precipitated under such conditions is a hydrolysate of an albumen protein having a molecular weight of about 5,000 or more. A smaller amount of this precipitate means that the molecular weight is reduced more, and the albumen hydrolysate according to the present invention comprises 60% by weight or more, preferably 65% by weight to 85% by weight, more preferably 70% by weight to 80% by weight of an albumen protein, and provides a gel which still retains heat gelation property at 90° C. and stands on its own. The rupture strength of the gel can be measured using a gel compression testing machine.

The amount of the albumen hydrolysate to be precipitated is adjusted within the above specific range, so that excellent emulsifiability, emulsion stability and heat coagulability are obtained.

Also, when the albumen hydrolysate according to the present invention is a dried product, a product obtained by adding 9 parts by weight of water to 1 part by weight of the dried product is used for the above measurement. Or, a dried product such as powder albumen is used as comparative albumen. A product obtained by dissolving the albumen hydrolysate and powder albumen in 9 times the amount of a solvent such as water can be measured as a sample.

Further, in an albumen hydrolysate having a moisture content of less than 90%, the amount of 0.4M TCA is appropriately changed in accordance with the moisture content thereof for measurement. Or, a product obtained by adding 9 parts by weight of water to 1 part by weight of the dried product obtained by removing moisture is used for the above measurement.

The amount of the precipitate can be measured by the following method.

Nine (9) g of a trichloroacetic acid (TCA) solution having a concentration of 0.4M is added to 1 g of the albumen hydrolysate according to the present invention, and the mixture is well stirred. Thereafter, the mixture is centrifuged by centrifugal force of 10,000×g for 20 minutes. The supernatant is wasted, and the precipitate is recovered and dried to measure the weight of the resultant dried product. Calculated is the proportion of the dry weight of the 0.4 M TCA precipitate of the albumen hydrolysate when the dry weight of the 0.4M TCA precipitate in 1 g of the albumen liquid used as a control is defined as 100%.

The albumen hydrolysate according to the present invention is a mixture of many kinds of protein hydrolysates having a molecular weight of 5,000 Daltons to 45,000 Daltons as measured by SDS-PAGE with a gradient gel having a polyacrylamide gel concentration of 5% to 20% in the presence of a reducing agent (2-mercaptoethanol) in accordance with a known method, and comprises a low-molecular weight protein decomposed product in which ovotransferrin of the albumen protein completely disappears and 40% or more of ovalbumin thereof disappears. Preferably, many protein decomposed products fall within the molecular weight ranging from 37,000 Daltons to 20,000 Daltons and the molecular weight ranging from 15,000 Daltons to 5,000 Daltons.

An albumen hydrolysate comprising a protein having a molecular weight falling within this range has heat coagulability and provides excellent emulsifiability and emulsion stability.

A process for producing the albumen hydrolysate according to the present invention comprises the step of hydrolyzing albumen with a protease at 55° C. to 65° C. and a pH of 6 to 9 for 0.5 hours to 4.0 hours.

The process further comprises the step of heating the hydrolyzed albumen at 85° C. to 95° C.

The albumen hydrolysate obtained through such steps has heat coagulability and excellent emulsifiability, emulsion stability.

The above hydrolysis conditions are defined in the same manner as above.

Specifically, the production process according to the present invention comprises, for example, the steps of: warming albumen to 45° C. to 60° C. before addition of a protease so as to attain a temperature at which an albumen protease inhibitor is hard to work and the heat coagulation of albumen would not start, avoiding the growth of bacteria in the hydrolysis reaction; hydrolyzing the above albumen; and carrying out heating treatment at 85° C. to 95° C. for 10 minutes to 30 minutes for further sterilization and enzyme deactivation.

The albumen hydrolysate according to the present invention forms a self-standing heated gel. Normal albumen liquid heated gels have a rupture strength of 70 g/cm$^2$ to 100 g/cm$^2$, whereas the albumen hydrolysate according to the present invention has a rupture strength of 5 g/cm$^2$ to 30 g/cm$^2$, preferably 5 g/cm$^2$ to 20 g/cm$^2$, more preferably 5 g/cm$^2$ to 10 g/cm$^2$.

The rupture strength of the heated gel is defined as the force (g/cm$^2$) required for destruction of the gel structure when a self-standing gel prepared in a sausage-like shape with a heat resistant casing tube is cut into a constant thickness and compressed at a constant speed by means of a cylindrical plunger in a food gel compression testing machine, and serves as the index of the hardness of the gel. A harder gel has a greater value of this rupture strength.

The rupture strength of the heated gel can be obtained from the gel rupture curve in which the compressive deformation rate of the gel is plotted on the abscissa axis and the pressure (load) applied to the plunger is plotted on the ordinate axis by means of a normal food gel compression testing machine.

For example, for a sample obtained by filling an albumen hydrolysate into a casing tube made of vinylidene chloride (folded width: 30 mm) and heating it at 90° C. for about 10 minutes to 30 minutes and then cooling it, the rupture curve is measured by means of a cylindrical plunger in a food gel compression testing machine, and the force (g/cm$^2$) required for destruction of the gel structure is measured as the rupture strength.

The albumen hydrolysate according to the present invention is characterized in that the absorbance (500 nm) of an emulsified liquid obtained by vertically agitating an albumen hydrolysate and an equal amount of salad oil for emulsification, collecting samples from the bottom part of the emulsified liquid immediately after the emulsification and after the elapse of 1 hour, and diluting the samples to 200 times with a 0.1% SDS solution, in accordance with the method of Pearce (Pearce K N and Kinsella J E: J. Agric. Food Chem., 26, 716-723, 1978) is 0.1 or more.

The emulsification activity is represented by the turbidity (absorbance at a wavelength of 500 nm) when the albumen hydrolysate according to the present invention and an oil such as salad oil are added in equal amount for emulsification, and a sample immediately after preparation of the emulsified liquid is diluted to 200 times with a 0.1% SDS solution (0.5% emulsified liquid) to dissolve the protein hydrolysate and micellize the salad oil. A higher value of this absorbance means higher emulsification activity.

When the above albumen hydrolysate is a dried product, a product obtained by adding 9 parts by weight of water to 1 part by weight of the dried product and emulsifying the resultant mixture with an equal amount of salad oil can be similarly measured. An albumen hydrolysate having a moisture content of less than 90% can be measured in the manner as descried above.

The emulsion stability is evaluated based on the turbidity of a 0.5% emulsified liquid similarly prepared from a sample collected from the bottommost part of an emulsified liquid allowed to stand still at a constant temperature for a constant time. A higher value of this turbidity, a greater rate thereof relative to the turbidity immediately after emulsification, or maintenance of high turbidity for a longer time after preparation means higher emulsion stability.

The oil is not particularly limited, and is preferably a vegetable oil such as salad oil, corn oil or cottonseed oil.

The absorbance at 500 nm can be measured by a known method.

For the albumen hydrolysate according to the present invention, the absorbance may be measured by collecting a sample from the bottom part of the emulsified liquid immediately after preparation, after 1-hour still standing at room temperature, and after 2-hour still standing at room temperature and diluting the sample to 200 times with a 0.1% SDS solution. The absorbance of the emulsified liquid immediately after preparation is normally 0.1 or more, preferably 0.2 or more, more preferably 0.3 or more, and further preferably 0.5 or more, most preferably 0.8 or more. In emulsion stability, the absorbance of the emulsified liquid after 1-hour still standing at room temperature is for example 45% or more, preferably 50% or more, more preferably 60% or more, most preferably 70% or more when the absorbance of the emulsified liquid immediately after preparation is defined as 100%.

In the present invention, the emulsifier may be the albumen hydrolysate according to the present invention itself, and may comprise other additives as an active ingredient. Also the emulsifier may comprise other emulsifiers.

Examples of the other additives mentioned above include protein materials such as albumen, soybean protein, casein, milk protein, plasma protein, collagen and gelatin; thickening polysaccharides such as carrageenan and dextrin; salts such as sodium nitrite and sodium chloride; saccharides such as sugar and starch; seasonings and phosphates.

Also, examples of the other emulsifiers include synthetic emulsifiers such as glycerol fatty acid ester, sorbitan fatty acid ester, propylene glycol fatty acid ester, sucrose fatty acid ester and polyglycerol fatty acid ester; and natural substance emulsifiers such as soybean lecithin, yolk lecithin, quillaja saponin and sodium caseinate.

The emulsifier in the present invention not only has excellent emulsifiability, but also is very highly safe, and thus can be safely used alone as an emulsifier for foods, beverages, feed, foods for fishes and shellfishes, cosmetics, medicaments and other various target products which require emulsifiability, or together with other emulsifiers.

The amount of the emulsifier in the present invention to be added to various target products is not particularly limited.

For example, the albumen hydrolysate according to the present invention (dry weight) is added in an amount of preferably 1 part to 20 parts by weight, more preferably 1 part to 10 parts by weight, relative to 100 parts by weight of a food.

Also, in the present invention, the emulsion stabilizer may be the albumen hydrolysate according to the present invention itself, and may comprise, as an active ingredient, other food materials such as starch, dextrin, gelatin, collagen, skimmed milk and whey protein. Also, the emulsion stabilizer may comprise other thickening stabilizers such as gum arabic, carrageenan, pectin, xanthan gum, gellan gum, guar gum and locust bean gum.

The amount of the emulsion stabilizer in the present invention to be added to various target products is, for example, the same amount as that of the above emulsifier.

A processed food comprising the albumen hydrolysate according to the present invention is also encompassed in the present invention.

Examples of the processed food in the present invention include processed foods that utilize the emulsifiability, emulsion stability and heating coagulability of the albumen hydrolysate.

For example, there are indicated: seasonings such as mayonnaise, dressing, aioli sauce and hollandaise sauce; desserts such as ice cream, mousse, yogurt and jellies; baked products such as cakes, bread, cream puffs and cookies; and beverages such as soup and drinks; and foods such as curry, stew, ham, sausage, kamaboko (white fish meat made into a seasoned paste, steamed, and typically formed into a semi-cylindrical shape over a strip of wood) and chikuwa (a kind of fish paste, shaped into a tubular form and grilled).

Especially, the albumen hydrolysate according to the present invention has emulsifying effect which normally is not possessed by albumen, but is possessed by yolk, and thus can be widely applied, as a substitute for whole egg, to various processed foods.

Also, functional lipids having a polyvalent unsaturated fatty acid such as DHA or EPA and fat soluble physiologically active substances such as steroid hormone, eicosanoid, fat soluble vitamins, carotenoid, lecithin and coenzyme Q10 may be arbitrarily incorporated in the albumen denatured product of the present invention. Also, the albumen denatured product of the present invention has good nutritional property which is comparable to that of breast milk protein and emulsion stabilizing effect, and thus can be applied to perfect nutritional supplement foods which comprise multivitamin, minerals, dietary fibers and/or functional lipids mixed and emulsified therein and are stable also for long-term storage.

Hereinafter, the present invention will be described in more detail by way of Examples which do not restrict the scope of the present invention.

EXAMPLES

Preparation Example 1 Preparation of Albumen Hydrolysate (Study on Hydrolysis Degree)

Products (500 g each) prepared by adding a 10% citric acid solution (24 ml) to 3 L of an albumen liquid (pH 9.0) and adjusting the pH of the mixture to pH 7.5 were warmed to 55° C., and a heat resistant proteolytic enzyme (Thermoase PC10F: 90,000 units/g, Amano Enzyme Inc.) was added thereto in an amount of 0.1%, 0.2%, 0.4% and 0.8%, respectively. The resultant mixtures were enzymatically decomposed while being stirred at 55° C. for 10 minutes. Then, the albumen liquids were subjected to temperature increase to 65° C., and enzymatically decomposed while being stirred for further 30 minutes. Thereafter, the albumen liquid was immediately subjected to temperature increase to 90° C., and held for 10 minutes for enzyme deactivation. The albumen hydrolysates after the enzyme deactivation were stirred to be homogenized, thereby preparing albumen hydrolysate samples 1 to 4. Incidentally, an albumen liquid was similarly manipulated without adding any enzyme, thereby preparing a heated albumen sample. In order to further increase the hydrolysis degree, the liquid temperature of the albumen hydrolysis sample 4 separately prepared with the above Thermoase added in an amount of 0.8% was decreased to 40° C., and Amano protease P (300,000 units/g) was added thereto in an amount of 0.5%. Hydrolysis was allowed to proceed at pH 7 for further 1 hour. The reaction liquid was heated at 90° C. for 10 minutes for enzyme deactivation, thereby preparing an albumen hydrolysate sample 5.

Test Example 1 Measurement of Emulsifiability

Ten (10) g of the albumen hydrolysate samples 1 to 5 and heated albumen sample prepared in Preparation Example 1, and a raw albumen liquid, respectively, and 10 g of salad oil were placed in a 50-ml-volume centrifugal tube with a plastic cap, and violently shaken up and down 100 times to be emulsified. Immediately after emulsification and after still standing for 60 minutes, 120 minutes and 240 minutes, 0.5 ml of an emulsified liquid was collected from the bottom of the respective centrifugal tubes, and diluted to 200 times with a 0.1% SDS solution, and then the turbidity was measured based on the absorbance at 500 nm (Pearce K N and Kinsella J E: J. Agric. Food Chem., 26, 716-723, 1978). Incidentally, a product prepared by emulsifying 10 g of water and 10 g of salad oil was used as a control. The results are shown in Table 1.

TABLE 1

| | | Albumen hydrolysate | | | | | | |
| | Heated albumen | Sample 1 | Sample 2 | Sample 3 | Sample 4 | Sample 5 | Raw albumen | Distilled water |
|---|---|---|---|---|---|---|---|---|
| | | | | | | | | |

Emulsifiability of albumen hydrolysates different in hydrolysis degree
Turbidity (absorbance at 500 nm)

| | Heated albumen | Sample 1 | Sample 2 | Sample 3 | Sample 4 | Sample 5 | Raw albumen | Distilled water |
|---|---|---|---|---|---|---|---|---|
| Still standing for 0 min. | 0.244 | 0.291 | 0.293 | 0.286 | 0.179 | 0.210 | 0.171 | 0.011 |
| Still standing for 60 min. | 0.063 | 0.306 | 0.313 | 0.275 | 0.161 | 0.030 | 0.005 | 0.005 |
| Still standing for 120 min. | 0.008 | 0.273 | 0.314 | 0.316 | 0.180 | 0.020 | 0.004 | 0.004 |
| Still standing for 240 min. | 0.005 | 0.239 | 0.264 | 0.317 | 0.162 | 0.016 | 0.004 | 0.006 |

The emulsifying capacity, in this test method, is evaluated based on the turbidity (absorbance at 500 nm) immediately after emulsification, namely, after still standing for 0 minute. Specifically, as the emulsified liquid collected from the bottom of the tube contains a larger amount of an oil, more micelles are formed in the presence of 0.1% SDS, resulting in higher turbidity. Distilled water had no emulsifying capacity, and the samples other than this had oil retaining capacity, i.e., emulsifying capacity though the degrees thereof were slightly different. Also, the emulsion stability can be evaluated based on the amount of the oil in the emulsified liquids collected, over time, from the bottom part of the emulsified liquid allowed to stand still, as a turbidity value. It was shown that, in the raw albumen, heated albumen and Sample 5, the turbidity almost disappeared after still standing for 60 minutes, and that they exhibited no emulsion stability. On the other hand, it was shown that Samples 1 to 4 were unchanged in turbidity even after 4-hour still standing, and had excellent emulsion stability.

As a result of visual observation of the emulsified products, the raw albumen, heated albumen and Sample 5 showed separation of the oil on the surfaces of the emulsified products from 2 hours after emulsification, but the emulsified products of Samples 1 to 4 showed no oil separation on the surfaces of those emulsified products even after 1 day.

Test Example 2 Evaluation of Heat Gelation Property

About 30 g was collected from the respective albumen liquids enzymatically decomposed at 65° C. for 20 minutes in the steps of Preparation Example 1, and immediately packed in polyvinylidene chloride casing tubes (Kureha Plastics Corporation, DB577R) having a folded width of 30 mm. The tubes were immersed in warm water set to 90° C., and held for 10 minutes after confirmation that the liquid temperature reached 90° C. Thereafter, the tubes were cooled in flowing water, thereby yielding Samples 1 to 4 for measurement of heat gelation property. Incidentally, an albumen liquid coagulated under similar heating conditions was used as a control sample. Incidentally, about 30 g of the hydrolyzed liquid after Amano protease P treatment of Sample 5 prepared in Preparation Example 1 was similarly packed in a casing tube, heated to 90° C., held for 10 minutes, and similarly cooled, thereby yielding a Sample 5 for measurement of heat gelation property.

Both ends of the casing tubes for the prepared samples 1 to 4 for measurement of heat gelation property and control sample were cut off with a cutter knife, and further a cut was made in the tubes to remove a sausage-shaped heated gel. This albumen gel was cut into a thickness of 10 mm to check whether the cylindrical gel stood on its own. As for the self-standing gels, the rupture strength of each gel was obtained by investigating the rupture deformation curve by means of a cylindrical plunger having a cross section of 1.0 cm$^2$ in a food gel compression testing machine (Texo Graph) under the condition: a plunger descending speed of 0.8 mm/sec. The rupture deformation curves of the control albumen gel and the prepared gels comprising an enzyme added in an amount of 0.1%, 0.2%, 0.4%, and 0.8% (Samples 1 to 4), respectively, are shown in FIG. 1 to FIG. 5. Also, the rupture strengths of the respective heated gels are shown in Table 2. Incidentally, the albumen hydrolysate sample 5 prepared in Preparation Example 1, even though similarly heated at 90° C. for 10 minutes, was not gelled, so that no self-standing gel could be obtained. Therefore, no measurement could be made.

TABLE 2

Heat gelation property of albumen hydrolysates different in hydrolysis degree

| | Albumen hydrolysate | | | | | |
| | Sample 1 | Sample 2 | Sample 3 | Sample 4 | Sample 5 | Albumen |
|---|---|---|---|---|---|---|
| Heated gel rupture strength (g/cm$^2$) | 22.8 | 21.8 | 9.9 | 7.1 | Not gelled | 74.0 |

Test Example 3 Measurement of Molecular Weight by SDS-PAGE

The albumen hydrolysate samples 1 to 5 and heated albumen sample prepared in Preparation Example 1 and the control sample (raw albumen liquid) were used to investigate the molecular weight distributions of their respective proteins by polyacrylic gel electrophoresis (PAGE) in the presence of sodium dodecyl sulfate (SDS). The electrophoresis device used was AE7350 manufactured by ATIO Co., Ltd., and the gel used was an existing gel of the same company, i.e., c-PAGEL (5% to 20%) gradient gel. Electrophoresis was conducted in accordance with the method of Laemnli et al. (Nature, 227, 680-685 (1970)). Incidentally, the samples were prepared so that all of them had a protein concentration of 0.33%, and 2 μL of the respective samples were applied to the respective lanes of the gel, and, after electrophoresis at 21 mA for 30 minutes, stained with the Coomassie Brilliant Blue dye.

Figure 6:
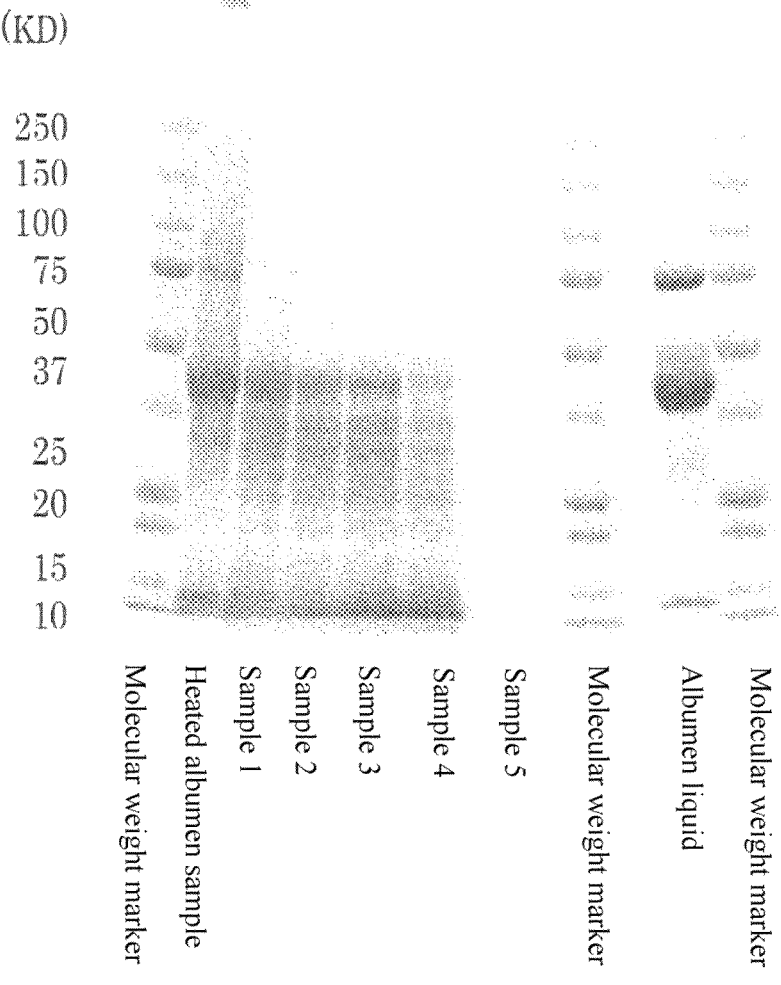
FIG. 6 shows the molecular weight distribution of the protein of the albumen hydrolysate prepared in Preparation Example 1 in polyacrylic gel electrophoresis.

The results are shown in FIG. 6. The protein of the albumen liquid was observed to show clear stained bands derived from ovotransferrin having a molecular weight of 77,000, ovalbumin having a molecular weight of 45,000, and lysozyme having a molecular weight of 14,300 from the high molecular weight side. On the other hand, the heated albumen sample showed stained bands derived from similar proteins, but the stained images were light and blurred. In the albumen hydrolysate samples 1 to 4, ovotransferrin of the albumen protein completely disappeared, and 50% or more of ovalbumin also disappeared. Instead, several characteristic stained bands derived from the hydrolysates appeared at a molecular weight between 37,000 and 20,000 and between 10,000 and 15,000. Sample 5 having the highest hydrolysis degree showed no stained band.

Preparation Example 2 Mass Preparation 1 of Albumen Hydrolysate

One hundred (100) Kg of an albumen liquid (pH 7.8) was waned by a warm water circulation jacket tank (200-L-volume), and 200 g of Thermoase PC10 was added thereto and dissolved therein at 55° C. The liquid was stirred for 10 minutes. Then, the liquid temperature was increased to 65±2° C., and the liquid was stirred for 30 minutes. Thereafter, the liquid temperature was held at 95±2° C. for 5 minutes, and enzyme deactivation was carried out also for heat sterilization. Then, the protease-treated hydrolyzed albumen was stirred to be homogenized with a homomixer, thereby preparing 97.2 Kg of an albumen hydrolysate (Sample 6).

Preparation Example 3 Mass Preparation 2 of Albumen Hydrolysate

Using a warm water circulation jacket tank (200-L-volume) as a balance tank, 200 Kg of an albumen liquid (pH 8.5) was circulated to a shell & tube type heat exchanger, STD model (Iwai Kikai Kogyo Co., Ltd.) at a flow rate of 150 Kg/h, and, when the temperature of the liquid within the balance tank reached 55° C., 200 g of Thermoase PC10 was added and dissolved. The temperature was retained at 55±2° C., and the liquid was circulated for 10 minutes. Then, the liquid temperature was rapidly increased to 65° C., and retained at 65±2° C., and the liquid was circulated for 30 minutes. Finally, the liquid temperature was retained at 95±2° C. for 5 minutes, and enzyme deactivation was carried out also for heat sterilization. Then, the liquid was rapidly cooled, thereby preparing 193 Kg of an albumen hydrolysate (Sample 7).

Preparation Example 4 Mass Preparation 3 of Albumen Hydrolysate

Using a warm water circulation jacket tank (200-L-volume) as a balance tank, 200 Kg of an albumen liquid (pH 8.5) was circulated to a Joule heating type sterilizer (Iwai Kikai Kogyo Co., Ltd.) at a flow rate of 150 Kg/h, and, when the temperature of the liquid within the balance tank reached 55° C., 200 g of Thermoase PC10 was added and dissolved. The temperature was retained at 55±2° C., and the liquid was circulated for 10 minutes. Then, the liquid temperature was rapidly increased to 65° C., and retained at 65±2° C., and the liquid was circulated for 30 minutes. Finally, the liquid temperature was retained at 95±2° C. for 5 minutes, and enzyme deactivation was carried out also for heat sterilization. Then, the liquid was rapidly cooled, thereby preparing 198 Kg of an albumen hydrolysate (Sample 8).

Test Example 4 Measurement of Emulsifiability of Mass-Prepared Sample

Using Samples 6 to 8 obtained in Preparation Examples 2 to 4 which were carried out as mass preparation of albumen hydrolysates, the emulsifiability was measured in a manner similar to in Test Example 1. The results are shown in Table 3.

TABLE 3

| Emulsifiability of albumen hydrolysates Turbidity (absorbance at 500 nm) | | | | |
|---|---|---|---|---|
| | Albumen hydrolysate | | | Raw |
| | Sample 6 | Sample 7 | Sample 8 | albumen |
| Still standing for 0 min. | 0.268 | 0.300 | 0.318 | 0.190 |
| Still standing for 60 min. | 0.236 | 0.288 | 0.324 | 0.004 |
| Still standing for 120 min. | 0.278 | 0.302 | 0.311 | 0.004 |
| Still standing for 240 min. | 0.288 | 0.298 | 0.319 | 0.004 |

Test Example 5 Evaluation of Heat Gelation Property

The albumen hydrolysate samples 6 to 8 obtained in Preparation Examples 2 to 4 were subjected to further enzyme treatment at 65±2° C. for 30 minutes. At the time of completion of the treatment, parts of the samples were collected to evaluate the heat gelation property by a method similar to in Test Example 2. The results are shown in Table 4.

TABLE 4

| Heat gelation property of albumen hydrolysates different in hydrolysis degree | | | |
|---|---|---|---|
| | Albumen hydrolysate | | |
| | Sample 6 | Sample 7 | Sample 8 |
| Heated gel rupture strength (g/cm²) | 16.8 | 12.2 | 15.5 |

Test Example 6 Measurement of Molecular Weight by SDS-PAGE

Figure 7:
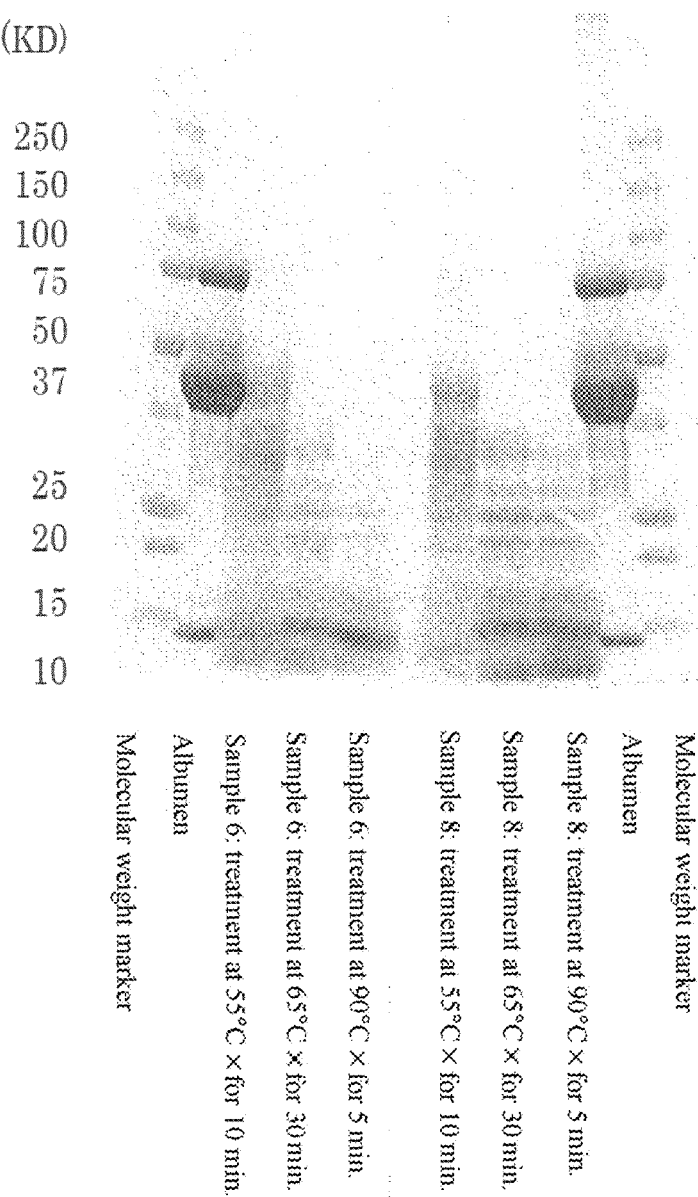
FIG. 7 shows the molecular weight distributions of the proteins of the albumen hydrolysates prepared in Preparation Examples 2 and 4 in polyacrylic gel electrophoresis.

The albumen hydrolysates (Samples 6 and 8) prepared in Preparation Examples 2 and 4 and the samples collected in the respective steps and control sample (raw albumen liquid) were used to investigate the molecular weight distributions of their respective proteins by a method similar to in Test Example 3. The results are shown in FIG. 7. In Samples 6 and 8, ovotransferrin and ovalbumin of the albumen proteins completely disappeared at the time of completion of the enzyme reaction at 65° C. Instead, several characteristic stained bands derived from the hydrolysate appeared at a molecular weight between 37,000 and 20,000 and between 5,000 and 15,000. In the albumen hydrolysates heated at 90° C. for 5 minutes for enzyme deactivation, the hydrolysis of Sample 6 proceeded farther, and the molecular weight of its albumen proteins was reduced more. This can be said to be due to the difference in heat history at the time of mass preparation. Namely, it is considered that the batch process might require much time for temperature increase, so that the heat resistant protease would act more.

Test Example 7 Measurement of Amount of Trichloroacetic Acid Precipitate

One (1) g of the albumen hydrolysate samples 1 to 5 and heated albumen sample prepared in Preparation Example 1, albumen hydrolysate samples 6 to 8 prepared in Preparation Example 2 to 4, and a raw albumen liquid as a control, respectively, were precisely weighed into a 15-mL-volume plastic centrifugal tube, and 9 g of a trichloroacetic acid (TCA) solution having a concentration of 0.4M was added thereto. The mixtures were well stirred, and centrifuged by centrifugal force of 10,000×g for 20 minutes. The supernatant was wasted, and the precipitate was recovered and dried at 105° C. for 3 hours to measure the weight of the resultant dried product. Calculated was the proportion of the dry weight of the 0.4 mol TCA precipitate of the respective samples when the dry weight of the 0.4M TCA precipitate in 1 g of the albumen liquid used as a control was defined as 100%.

The results are shown in Table 5.

TABLE 5

| | Albumen hydrolysate | | | | | | | | |
| | Sample 1 | Sample 2 | Sample 3 | Sample 4 | Sample 5 | Sample 6 | Sample 7 | Sample 8 | Raw albumen |
|---|---|---|---|---|---|---|---|---|---|
| Dry weight of TCA precipitate | 0.149 | 0.133 | 0.128 | 0.112 | 0 | 0.103 | 0.104 | 0.106 | 0.168 |
| Same as above (%) | 82.9 | 79.3 | 76.2 | 66.8 | 0 | 61.4 | 62.0 | 63.2 | 100.0 |

Preparation Example 5 Preparation of Albumen Hydrolysate (Study on Hydrolysis Time)

Eight (8) ml of a 10% citric acid solution was added to 1,000 ml of an albumen liquid to adjust the pH of the mixture to pH 7.5. The mixture was warmed to 55° C., and a heat resistant proteolytic enzyme (Thermoase PC10F: 90,000 units/g, Amano Enzyme Inc.) was added thereto in an amount of 0.4%. The mixture was enzymatically decomposed while being stirred at 55° C. for 10 minutes. Then, the temperature of the albumen liquids was increased to 65° C., and enzymatic decomposition was carried out with stirring while the hydrolysis time was changed to 0 minute, 30 minutes, 1 hour, 2 hours, 4 hours, and 8 hours. Then, 30 g of the respective albumen hydrolyzed liquids were packed in polyvinylidene chloride casing tubes (Kureha Plastics Corporation DB577R) having a folded width of 30 mm for each enzyme reaction time. The tubes were immersed in warm water set to 90° C., and held for 10 minutes after confirmation that the liquid temperature reached 90° C. Thereafter, the tubes were cooled in flowing water, thereby yielding albumen hydrolysate samples 9 to 14.

Samples 9 to 14 and a raw albumen liquid as a control were used to measure the rupture strengths of the respective samples by a method similar to in Test Example 2. Then, the emulsifiability and emulsion stability were evaluated by the same methods as in Test Example 1. Also, the proportion of the dry weight of the 0.4 mol TCA precipitates of each of the samples was calculated by the same method as in Test Example 7. The results are summarized in Table 6.

TABLE 6

| Hydrolysis time and heat gelation property, emulsifiability and TCA precipitate dry weight % of albumen hydrolysates | | | | | | | |
|---|---|---|---|---|---|---|---|
| | Albumen hydrolysate (Amount of enzyme added 0.4%) | | | | | | Raw albumen |
| | Sample 9 | Sample 10 | Sample 11 | Sample 12 | Sample 13 | Sample 14 | |
| Heated gel rupture strength (g/cm$^2$) | 12.2 | 11.3 | 9.8 | 7.4 | 6.3 | Not gelled | 79.8 |
| Emulsifiability (500 nm) Still standing for 0 min. | 0.268 | 0.287 | 0.245 | 0.221 | 0.178 | 0.189 | 0.223 |
| Still standing for 60 min. | 0.277 | 0.248 | 0.289 | 0.175 | 0.131 | 0.081 | 0.004 |
| Still standing for 120 min. | 0.223 | 0.247 | 0.256 | 0.135 | 0.138 | 0.008 | 0.004 |
| Still standing for 240 min. | 0.243 | 0.219 | 0.233 | 0.117 | 0.115 | 0.004 | 0.004 |
| TCA precipitate dry weight | 0.144 | 0.132 | 0.122 | 0.113 | 0.103 | 0.09 | 0.168 |
| Same as above (%) | 85.7% | 78.5% | 72.7% | 67.0% | 61.4% | 51.3% | 100.0% |

As a result of the study on the time of hydrolysis at 65° C. by adding a proteolytic enzyme (Thermoase PC10F: 90,000 units/g, Amano Enzyme Inc.) in an amount of 0.4%, the heat gelation property at 90° C. existed in the case where the hydrolysis time was up to 4 hours, but the rupture gel strength became weaker as the hydrolysis time was longer. The heat gelation property at 90° C. of the samples hydrolyzed for 8 hours disappeared, and the TCA precipitate was also decreased from 85.7% to 61.3% as the hydrolysis time was longer. This results from proceeding of the hydrolysis of the albumen protein and thus increase in low molecular weight peptides and amino acids which would not be precipitated with 0.4% TCA. Incidentally, the emulsion stability was reduced little by little in the case where the hydrolysis time was up to 4 hours, but the emulsion stability of the samples hydrolyzed for 8 hours was sharply reduced.

Preparation Example 6 Preparation 1 of Albumen Hydrolysate (Study on Enzyme Deactivation Temperature)

Products (500 g each) prepared by adding a 10% citric acid solution (24 ml) to 3 L of an albumen liquid (pH 9.0) and adjusting the pH of the mixture to pH 7.5 were warmed to 55° C., and a heat resistant proteolytic enzyme (Thermoase PC10F: 90,000 units/g, Amano Enzyme Inc.) was added thereto in an amount of 0.2%. The resultant mixtures were enzymatically decomposed while being stirred at 55° C. for 10 minutes. Then, the albumen liquids were subjected to temperature increase to 65° C., and enzymatically decomposed while being further stirred for 30 minutes (this product was defined as an albumen hydrolysate sample 15). Thereafter, the albumen liquids were further warmed to increase the albumen liquid temperature to 80° C., 90° C. and 100° C., respectively, and held for 10 minutes for enzyme deactivation. The albumen hydrolysates after the enzyme deactivation were stirred to be homogenized, thereby preparing albumen hydrolysate samples 16 to 18. The conditions for treating the samples are briefly indicated below.
Sample 15: (treatment at 55° C. for 10 minutes)→(treatment at 65° C. for 30 minutes)
Sample 16: (treatment at 55° C. for 10 minutes)→(treatment at 65° C. for 30 minutes)→(treatment at 80° C. for 10 minutes)
Sample 17: (treatment at 55° C. for 10 minutes)→(treatment at 65° C. for 30 minutes)→(treatment at 90° C. for 10 minutes)
Sample 18: (treatment at 55° C. for 10 minutes)→(treatment at 65° C. for 30 minutes)→(treatment at 100° C. for 10 minutes)

Preparation Example 7 Preparation 2 of Albumen Hydrolysate (Study on Enzyme Deactivation Temperature)

A proteolytic enzyme (Thermoase PC10F: 90,000 units/g, Amano Enzyme Inc.) was added in an amount of 0.4% to prepare albumen hydrolysate samples 19 to 22 in a manner similar to in Preparation Example 6. The conditions for treating the samples are briefly indicated below.
Sample 19: (treatment at 55° C. for 10 minutes)→(treatment at 65° C. for 30 minutes)
Sample 20: (treatment at 55° C. for 10 minutes)→(treatment at 65° C. for 30 minutes)→(treatment at 80° C. for 10 minutes)
Sample 21: (treatment at 55° C. for 10 minutes)→(treatment at 65° C. for 30 minutes)→(treatment at 90° C. for 10 minutes)
Sample 22: (treatment at 55° C. for 10 minutes)→(treatment at 65° C. for 30 minutes)→(treatment at 100° C. for 10 minutes)

Preparation Example 8 Preparation 3 of Albumen Hydrolysate (Study on Enzyme Deactivation Temperature)

A proteolytic enzyme (Thermoase PC10F: 90,000 units/g, Amano Enzyme Inc.) was added in an amount of 0.8% to prepare albumen hydrolysate samples 23 to 26 in a manner similar to in Preparation Example 6. The conditions for treating the samples are briefly indicated below.
Sample 23: (treatment at 55° C. for 10 minutes)→(treatment at 65° C. for 30 minutes)
Sample 24: (treatment at 55° C. for 10 minutes)→(treatment at 65° C. for 30 minutes)→(treatment at 80° C. for 10 minutes)
Sample 25: (treatment at 55° C. for 10 minutes)→(treatment at 65° C. for 30 minutes)→(treatment at 90° C. for 10 minutes)
Sample 26: (treatment at 55° C. for 10 minutes)→(treatment at 65° C. for 30 minutes)→(treatment at 100° C. for 10 minutes)

Test Example 8 Measurement of Emulsifiability (Study on Enzyme Deactivation Temperature)

Two (2) g of the respective albumen hydrolysate samples 15 to 26 prepared in Preparation Examples 6 to 8, 3 g of olive oil and 1 g of water were placed in 50-ml-volume centrifugal tubes with a plastic cap, and violently shaken up and down 100 times to be emulsified. Immediately after emulsification and after still standing for 120 minutes, 0.5 ml of an emulsified liquid was collected from the bottom of the respective centrifugal tubes, and diluted to 200 times with a 0.1% SDS solution, and then the turbidity was measured based on the absorbance at 500 nm (Pearce K N and Kinsella J E: J. Agric. Food Chem., 26,716-723, 1978). Incidentally, a product prepared by emulsifying 2 g of raw albumen, 1 g of water and 3 g of olive oil was used as a control. The results are shown in Table 7.

TABLE 7

| | Raw albumen | Sample 15 | Sample 16 | Sample 17 | Sample 18 | Sample 19 | Sample 20 | Sample 21 | Sample 22 |
|---|---|---|---|---|---|---|---|---|---|
| Amount of enzyme added | — | 0.2% | | | | 0.4% | | | |
| Still standing for 0 min. (absorbance at 500 nm) | 0.249 | 0.342 | 0.584 | 0.553 | 0.436 | 0.355 | 0.41 | 0.616 | 0.542 |

TABLE 7-continued

| Still standing for 120 min. (absorbance at 500 nm) | 0.007 | 0.06 | 0.565 | 0.483 | 0.388 | 0.03 | 0.355 | 0.602 | 0.449 |
|---|---|---|---|---|---|---|---|---|---|

| | Sample 23 | Sample 24 | Sample 25 | Sample 26 |
|---|---|---|---|---|
| Amount of enzyme added | | 0.8% | | |
| Still standing for 0 min. (absorbance at 500 nm) | 0.346 | 0.372 | 0.464 | 0.494 |
| Still standing for 120 min. (absorbance at 500 nm) | 0.016 | 0.172 | 0.383 | 0.4 |

The samples having the enzyme deactivated showed good emulsifiability 120 minutes after emulsification, as compared with the samples having the enzyme not deactivated. Also, the emulsifiability of the samples when the amount of the enzyme added was 0.2% or 0.4% was good as compared with the emulsifiability of the samples when the amount of the enzyme added was 0.8%.

Preparation Example 9 Preparation 1 of Albumen Hydrolysate (Study on Enzyme Reaction Time)

Products (500 g each) prepared by adding a 10% citric acid solution (24 ml) to 3 L of an albumen liquid (pH 9.0) and adjusting the pH of the mixture to pH 6.0 were warmed to 50° C., and protease M "AMANO" SD (40,000 units/g, Amano Enzyme Inc.) was added as a proteolytic enzyme thereto in an amount of 0.1%. The resultant mixtures were enzymatically decomposed at 50° C. for 30 minutes, 45 minutes, 60 minutes and 90 minutes, respectively. Then, the albumen liquids were further warmed to increase the albumen liquid temperature to 75° C., and held for 5 minutes for enzyme deactivation, thereby preparing albumen hydrolysate samples 27 to 30. The conditions for treating the samples are briefly indicated below.

Sample 27: (treatment at 50° C. for 30 minutes)→(treatment at 75° C. for 5 minutes)
Sample 28: (treatment at 50° C. for 45 minutes)→(treatment at 75° C. for 5 minutes)
Sample 29: (treatment at 50° C. for 60 minutes)→(treatment at 75° C. for 5 minutes)
Sample 30: (treatment at 50° C. for 90 minutes)→(treatment at 75° C. for 5 minutes)

Preparation Example 10 Preparation 2 of Albumen Hydrolysate (Study on Enzyme Reaction Time)

Protease M "AMANO" SD (40,000 units/g, Amano Enzyme Inc.) was added as a proteolytic enzyme in an amount of 0.2%, thereby preparing albumen hydrolysate samples 31 to 34 in a manner similar to in Preparation Example 9. The conditions for treating the samples are briefly indicated below.

Sample 31: (treatment at 50° C. for 30 minutes)→(treatment at 75° C. for 5 minutes)
Sample 32: (treatment at 50° C. for 45 minutes)→(treatment at 75° C. for 5 minutes)
Sample 33: (treatment at 50° C. for 60 minutes)→(treatment at 75° C. for 5 minutes)
Sample 34: (treatment at 50° C. for 90 minutes)→(treatment at 75° C. for 5 minutes)

Test Example 9 Measurement of Emulsifiability (Study on Enzyme Reaction Time)

In 50-ml-volume centrifugal tubes with a plastic cap, placed were 0.8 g of the respective albumen hydrolysate samples 27 to 34 prepared in Preparation Examples 9 to 10, 3 g of olive oil and 1 g of water. They were violently shaken up and down 100 times to be emulsified. Immediately after emulsification, 0.5 ml of an emulsified liquid was collected from the bottom of the respective centrifugal tubes, and diluted to 200 times with a 0.1% SDS solution, and then the turbidity was measured based on the absorbance at 500 nm (Pearce K N and Kinsella J E: J. Agric. Food Chem., 26, 716-723, 1978). The results are shown in Table 8.

TABLE 8

| | Sample 27 | Sample 28 | Sample 29 | Sample 30 | Sample 31 | Sample 32 | Sample 33 | Sample 34 |
|---|---|---|---|---|---|---|---|---|
| Amount of enzyme added | | 0.1% | | | | 0.2% | | |
| Still standing for 0 min. (absorbance at 500 nm) | 0.769 | 0.650 | 0.854 | 0.924 | 0.861 | 0.937 | 0.982 | 1.220 |

Preparation Example 11 Preparation 1 of Albumen Hydrolysate (Study on Enzyme Deactivation Temperature)

Products (500 g each) prepared by adding a 10% citric acid solution (24 ml) to 3 L of an albumen liquid (pH 9.0) and adjusting the pH of the mixture to pH 6.0 were warmed to 50° C., and protease M "AMANO" SD (40,000 units/g, Amano Enzyme Inc.) was added as a proteolytic enzyme thereto in an amount of 0.1%. The resultant mixtures were enzymatically decomposed while being stirred at 50° C. for 60 minutes. Then, the albumen liquids were further warmed to increase the albumen liquid temperature to 80° C., 85° C. and 90° C., respectively, and held for 5 minutes for enzyme deactivation, thereby preparing albumen hydrolysate samples 35 to 37. The conditions for treating the samples are briefly indicated below.

Sample 35: (treatment at 50° C. for 60 minutes)→(treatment at 80° C. for 5 minutes)

Sample 36: (treatment at 50° C. for 60 minutes)→(treatment at 85° C. for 5 minutes)

Sample 37: (treatment at 50° C. for 60 minutes)→(treatment at 90° C. for 5 minutes)

Preparation Example 12 Preparation 2 of Albumen Hydrolysate (Study on Enzyme Deactivation Temperature)

Protease M "AMANO" SD (40,000 units/g, Amano Enzyme Inc.) was added as a proteolytic enzyme in an amount of 0.2%, thereby preparing albumen hydrolysate samples 38 to 40 in a manner similar to in Preparation Example 9. The conditions for treating the samples are briefly indicated below.

Sample 38: (treatment at 50° C. for 60 minutes)→(treatment at 80° C. for 5 minutes)

Sample 39: (treatment at 50° C. for 60 minutes)→(treatment at 85° C. for 5 minutes)

Sample 40: (treatment at 50° C. for 60 minutes)→(treatment at 90° C. for 5 minutes)

Test Example 10 Measurement of Emulsifiability (Study on Enzyme Deactivation Time)

In 50-ml-volume centrifugal tubes with a plastic cap, placed were 0.8 g of the respective albumen hydrolysate samples 35 to 40 prepared in Preparation Examples 11 and 12, 3 g of olive oil and 1 g of water. Then, they were violently shaken up and down 100 times to be emulsified. Immediately after emulsification, 0.5 ml of an emulsified liquid was collected from the bottom of the respective centrifugal tubes, and diluted to 200 times with a 0.1% SDS solution, and then the turbidity was measured based on the absorbance at 500 nm (Pearce K N and Kinsella J E: J. Agric. Food Chem., 26,716-723, 1978). The results are shown in Table 9.

TABLE 9

|  | Sample 35 | Sample 36 | Sample 37 | Sample 38 | Sample 39 | Sample 40 |
|---|---|---|---|---|---|---|
| Amount of enzyme added |  | 0.1% |  |  | 0.2% |  |
| Still standing for 0 min. (absorbance at 500 nm) | 0.874 | 1.051 | 1.091 | 1.145 | 1.209 | 1.154 |

Food Example 1 Albumen Mayonnaise

Fifty (50) g of vinegar was added to and mixed with 250 g of the albumen hydrolysate prepared in Preparation Example 2, and 10 g of common salt, 5 g of mustard and 2.5 g of pepper were mixed therewith. Further, 550 g of salad oil was added little by little, and the mixture was stirred to be emulsified, thereby producing albumen mayonnaise using the albumen hydrolysate as an emulsifier.

Food Example 2 Egg Ice Cream

Eighty (80) g of raw yolk and 100 g of sugar were placed in a stainless bowl, and mixed thoroughly until the mixture turned whitish. Three hundred (300) g of the albumen hydrolysate prepared in Preparation Example 2 was homogenized by a homomixer and, at the same time, foamed so that the volume was increased 1.5 times to 2.0 times. The mixture of yolk and sugar was added to this, and the mixture was heated by low heat until the fishy smell of yolk was eliminated (until the temperature reached about 80° C.). After cooling, several drops of vanilla essence was added, and the product was placed in a freezer at −20° C. to be frozen while being stirred once per hour, thereby producing egg ice cream.

Food Example 3 Sterilized Egg Liquid for Tamago Kake Gohan (Rice with Raw Egg)

Shelled eggs were subjected to an egg breaker to separate yolk from albumen while preventing breakage of the yolk membrane. One raw yolk (about 20 g) was placed in a sterilized plastic container, and 40 g of the albumen hydrolysate prepared in Preparation Example 4 and kept to a temperature of 80° C. was added from the above thereof. Immediately, a plastic seal was thermally fused to the plastic container aseptically to cap the container. By this method, produced was a sterilized egg liquid for tamago kake gohan in which the bacteria on the yolk membrane were heat-sterilized with the albumen hydrolysate at 80° C. and which contained whole yolk.

Food Example 4 Albumen Nutritional Food (Drink Base)

Six hundred (600) g of the albumen hydrolysate prepared in Preparation Example 4 was heated to 90° C. while being stirred to be homogenized by a homomixer, and 20 g of sugar and 66 g of dietary fibers (guar gum enzymatically decomposed product) were mixed therewith and dissolved therein. This liquid mixture was cooled to room temperature, and 1 g of vitamin premix type RD-2001 (multi-vitamin) was added and mixed, thereby producing a drink base of an albumen nutritional food.

To this drink base, various beverages, soup, broth and/or bouillon as flavors, or olive oil and/or refined fish oil containing an unsaturated fatty acid as functional materials was/were added in an equal to half amount, and the mixture was stirred to homogenized, thereby obtaining a nutritional drink prepared based on the albumen hydrolysate comprising good amino acids as constituents and providing excellent digestive absorbency due to heat denaturation.

Food Example 5 Albumen Nutritional Food (Gel Base)

Six hundred (600) g of the albumen hydrolysate prepared in Preparation Example 4 was heated to 90° C. while being stirred to be homogenized by a homomixer, and 20 g of sugar, 6 g of low methoxyl pectin and 60 g of dietary fibers (guar gum enzymatically decomposed product) were mixed therewith and dissolved therein. This liquid mixture was cooled to room temperature, and 1 g of vitamin premix type RD-2001 (multi-vitamin) was added and mixed, thereby producing a gel base of the albumen nutritional food.

Three hundred (300) g of milk was added to this gel base for thickening and gelation, thereby obtaining an albumen nutritional gel prepared based on an albumen hydrolysate comprising good amino acids as constituents and providing excellent digestive absorbency due to heat denaturation. In the meantime, various beverages, jams and boiled azuki bean can also be appropriately added and mixed as flavors.

Food Example 6 Egg Whipping Cream

One (1) Kg of yolk was added to and mixed with 2 Kg of the albumen hydrolysate prepared in Preparation Example 3 for emulsification. Then, 150 g of trehalose and several drops of vanilla essence were added, and the mixture was further homogenized by a homomixer and, at the same time, foamed so that the volume was increased 1.5 times to 2.0 times, thereby preparing 3.15 Kg of egg whipping cream for shortcakes, roll cakes and cream puffs.

The invention claimed is:

1. A process for producing an albumen hydrolysate by hydrolysis of raw albumen with a protease comprising either (a) hydrolyzing the raw albumen at 45° C. to 60° C. for 10 minutes to 1 hour; or (b) hydrolyzing the raw albumen at 45° C. to 70° C. for 0.5 hour to 1 hour at a pH of 6 to 9,
   wherein the hydrolysate is a self-standing heated gel,
   wherein hydrolyzing the raw albumen produces the albumen hydrolysate having high-molecular-weight protein decomposition products having a molecular weight of 5,000 to 15,000 Daltons or 20,000 to 37,000 Daltons.

2. The process according to claim 1, wherein the raw albumen is hydrolyzed at 45° C. to 60° C. for 10 minutes to 1 hour, the process further comprising hydrolyzing the raw albumen at 60° C. to 80° C. for 0.5 hours to 2 hours at a pH of 6 to 9.

3. The process according to claim 1, wherein the hydrolysate is further heated at 75° C. to 100° C. for 5 minutes to 30 minutes.

4. The process according to claim 1 wherein the dry weight of a precipitate formed by adding nine times the amount of 0.4 M trichloroacetic acid (TCA) to the raw albumen hydrolysate which is obtained by the hydrolysis of raw albumen with a protease is 60% or more relative to the dry weight of raw albumen treated in the same manner.

5. The process according to claim 1, wherein the protease is a protease extracted from a microorganism belonging to the genus *Bacillus* or *Aspergillus*.

6. The process according to claim 1, wherein the microorganism belonging to the genus *Bacillus* is *Bacillus stearothermophilus*.

7. The process according to claim 1, wherein the microorganism belonging to the genus *Aspergillus* is *Aspergillus oryzae*.

8. An albumen hydrolysate which is obtained by the process according to claim 1.

9. The process according to claim 1, comprising:
   (a) hydrolyzing the raw albumen at 45° C. to 60° C. for 10 minutes to 30 minutes; and
   (b) hydrolyzing the raw albumen at 60° C. to 70° C. for 0.5 hours to 1 hour at a pH of 6 to 9.

10. The process according to claim 1, wherein the hydrolysate is further heated at 75° C. to 100° C. for 5 minutes to 10 minutes.

11. The process according to claim 1, wherein ovotransferrin disappears completely, and ovalbumin disappears by 40% or more.

* * * * *